United States Patent [19]

Fleischmann et al.

[11] Patent Number: 5,455,361
[45] Date of Patent: Oct. 3, 1995

[54] PROCESS FOR PREPARING KETENE ACETALS

[75] Inventors: Gerald Fleischmann; Herbert Eck; Hermann Petersen, all of Burghausen; Siegfried Pflaum, Burgkirchen, all of Germany

[73] Assignee: Wacker-Chemie GmbH, Munich, Germany

[21] Appl. No.: 120,965

[22] Filed: Sep. 13, 1993

[30] Foreign Application Priority Data

Sep. 17, 1992 [DE] Germany .................. 42 31 193.4

[51] Int. Cl.⁶ .................. C07D 321/06; C07D 319/06; C07D 317/08; C07C 43/303
[52] U.S. Cl. .................. 549/347; 549/369; 549/430; 568/596
[58] Field of Search .................. 568/596; 549/347, 549/369, 430

[56] References Cited

U.S. PATENT DOCUMENTS

| | | |
|---|---|---|
| 3,431,281 | 3/1969 | Saways . |
| 4,603,224 | 7/1986 | Ruland et al. . |
| 5,144,046 | 9/1992 | Mathur .................. 549/347 |
| 5,396,002 | 3/1995 | Reed et al. .................. 570/228 |

FOREIGN PATENT DOCUMENTS

| | | |
|---|---|---|
| 0095182 | 11/1983 | European Pat. Off. . |
| WO92/14722 | 9/1992 | WIPO . |

OTHER PUBLICATIONS

H. A. Davis and R. K. Brown, Canadian Journal of Chemistry 49, 2321–2335, 1971.
Houben–Weyl vol. 7/4, 4th Ed., Stuttgart 1968, pp. 340–355.
Bailey, W. J., "Ring–Opening Polymerisation," *Comprehensive Polymer Science,* vol. 3, Pergamon Press 1989, pp. 285–319.
CA 113 (18): 153070z.

*Primary Examiner*—Joseph L. Schofer
*Assistant Examiner*—Wu C. Cheng
*Attorney, Agent, or Firm*—Collard & Roe

[57] ABSTRACT

The invention relates to a process for preparing ketene acetals by dehydrohalogenation of 2-haloaldehyde acetals. If the 2-haloaldehyde acetal is open chain, the dehydrohalogenation is carried out in the presence of an alkali metal hydroxide or alkaline earth metal hydroxide and a phase transfer catalyst and/or a secondary or tertiary alcohol or a secondary or tertiary diol. If the 2-haloaldehyde acetals is cyclic, the dehydrohalogenation is carried out in the presence of an alkali metal hydroxide or alkaline earth metal hydroxide and a phase transfer catalyst and with or without a secondary or tertiary alcohol or a secondary or tertiary diol, or carried out in the presence of an alkali metal hydroxide or alkaline earth metal hydroxide and a secondary or tertiary diol. The ketene acetals which can be prepared by the process of the invention serve as intermediates in organic synthesis and are suitable as monomers or comonomers in free radical polymerization for the production of biodegradable plastics.

31 Claims, No Drawings

PROCESS FOR PREPARING KETENE ACETALS

BACKGROUND OF THE INVENTION

1. Field of the Invention

The present invention relates to a process for preparing ketene acetals by dehydrohalogenation of 2-haloaldehyde acetals.

2. The Prior Art

It is known that ketene acetals can be obtained from the corresponding 2-haloaldehyde acetals by elimination of hydrogen halide with the aid of alkoxides or amine bases. Both Houben-Weyl Vol. 7/4, 4th Ed., Stuttgart 1968, p. 340, and W. J. Bailey, "Ring-Opening Polymerisation," *Comprehensive Polymer Science*, Vol. 3, Pergamon Press 1989, pp. 283–326, describe hydrogen bromide elimination by means of potassium tert.-butoxide. C.A. 113 (18):153070 discloses the dehydrobromination in the presence of potassium tert.-butoxide and a phase transfer catalyst. The dehydrochlorination of 2-chloromethyl-1,3-dioxolane by means of sodium or potassium in liquid ammonia is described in U.S. Pat. No. 3,431,281. These procedures have the disadvantages that in these methods only the more reactive and also more expensive 2-bromoaldehyde acetals can be used as starting compounds. In addition, the bases which can be used are the relatively expensive (for synthesis on an industrial scale), alkali or alkaline earth metal alkoxides or alkali metals dissolved in liquid ammonia.

WO-A 92/14722 relates to a process for the dehydrohalogenation of halogenated cyclic ketene acetals such as 2-chloromethyl-1,3-dioxepane with alkali or alkaline earth metal hydroxides in the presence of an inert alcohol such as 2-butanol. This procedure has the disadvantage of the low yields (low selectivity and by-products from aqueous work-up) which are obtained in this process after purification, which is complicated into the bargain, of the crude product by fractional distillation in the presence of an organic solvent and an amine.

SUMMARY OF THE INVENTION

It is an object of the present invention to provide a process by which ketene acetals can be obtained both from 2-bromoaldehyde acetals start material and from the less expensive but less reactive 2-chloroaldehyde acetals.

It is another object of the present invention to provide a process for this synthesis which will furthermore avoid the use of relatively expensive bases such as alkali metal alkoxides or alkaline earth metal alkoxides or alkali metals dissolved in liquid ammonia and produce the ketene acetal in good yields without complicated purification procedures.

The invention relates to a process for preparing ketene acetals by dehydrohalogenation of 2-haloaldehyde acetals, wherein the dehydrohalogenation (a) in the case of open chain 2-haloaldehyde acetals is carried out in the presence of an alkali metal hydroxide or alkaline earth metal hydroxide and a phase transfer catalyst and/or a secondary or tertiary alcohol or a secondary or tertiary diol, and (b) in the case of cyclic 2-haloaldehyde acetals is carried out in the presence of an alkali metal hydroxide or alkaline earth metal hydroxide and a phase transfer catalyst and with or without a secondary or tertiary alcohol or a secondary or tertiary diol, or carried out in the presence of an alkali metal hydroxide or alkaline earth metal hydroxide and a secondary or tertiary diol.

The process is suitable for preparing ketene acetals of the formula

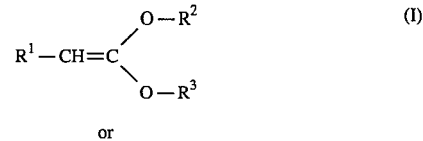

or

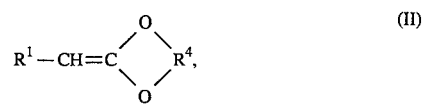

in which $R^1$ can be hydrogen, a straight chain, branched or cyclic alkyl radical having from 1 to 18 carbon atoms, preferably from 1 to 4 carbon atoms; an alkenyl radical having from 2 to 18 carbon atoms; an aryl radical having from 6 to 12 carbon atoms; or an aralkyl radical having from 7 to 12 carbon atoms, and $R^2$ and $R^3$ are the same or different, and can be an alkyl radical having from 1 to 18 carbon atoms, preferably from 1 to 4 carbon atoms; an alkenyl radical having from 2 to 18 carbon atoms; an aryl radical having from 6 to 12 carbon atoms; or an aralkyl radical having from 7 to 12 carbon atoms; and $R^4$ is a radical $(CR^5R^6)_m$, with m being an integer of from 2 to 5, in which $R_5$ and $R_6$ may be the same or different and are hydrogen, a straight chain or branched alkyl radical having from 1 to 4 carbon atoms, an alkenyl radical having from 2 to 4 carbon atoms, an aryl radical having from 6 to 12 carbon atoms, or an aralkyl radical having from 7 to 12 carbon atoms.

Particularly preferred are ketene acetals of the above-mentioned formulae, in which $R^1$ is hydrogen, $R^2$ and $R^3$ are the same and are an alkyl radical having from 1 to 4 carbon atoms, and $R^4$ is a —$(CH_2)_4$— radical.

Suitable starting materials for the process of the invention are 2-haloaldehyde acetals of the formula

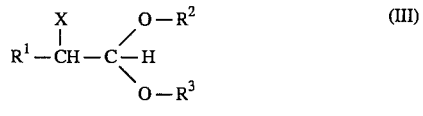

or

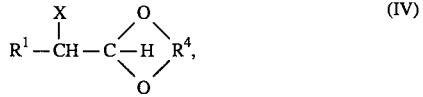

in which $R^1$, $R^2$, $R^3$ and $R^4$ are the same as defined above and X is Cl or Br. Preference is given to haloaldehyde acetals of the formula (III) or (IV) having X being Cl. In particular, haloaldehyde acetals of the formula (III) or (IV) having X being Cl, in which $R^1$ is hydrogen, $R^2$ and $R^3$ are the same and are an alkyl radical having from 1 to 4 carbon atoms and $R^4$ is a —$(CH_2)_4$—radical, are used. If the 2-haloaldehyde acetals mentioned are not readily available commercially, they can be prepared by generally known synthetic routes: starting with the corresponding aldehydes, the 2-haloaldehydes can be obtained by acid- or base-catalyzed halogenation. The 2-haloaldehyde acetals are preferably obtained by acid-catalyzed reaction with the corresponding alcohols.

The dehydrohalogenation is carried out in the presence of alkali metal hydroxides or alkaline earth metal hydroxides such as LiOH, NaOH, KOH, CsOH, Ca(OH)$_2$, Sr(OH)$_2$, Ba(OH)$_2$. Preferably, potassium hydroxide is used for the dehydrohalogenation. The molar ratio of 2-haloaldehyde acetal to alkali metal hydroxide or alkaline earth metal hydroxide is from 1:1 to 1:25, preferably from 1:1 to 1:5, particularly preferably from 1:2 to 1:4.

Suitable phase transfer catalysts for the process of the invention are, for example, polyethylene glycol dialkyl ethers, polyethylene glycol aryl aralkyl ethers such as TRITON® CF10, polyethylene glycol alkyl aryl ethers, crown ethers, tris-[2-(2-methoxyethoxy)ethyl]amine, tetraalkylammonium salts and aralkyltrialkylammonium salts. Preference is given to using polyethylene glycol dialkyl ethers, TRITON® CF10 and tris-[2-(2-methoxy-ethoxy)ethyl]amine (TDA1). The phase transfer catalysts are used in a weight ratio of phase transfer catalyst to 2-haloaldehyde acetal of from 0.001:1 to 1:1, preferably from 0.01:1 to 0.2:1.

Suitable additional catalysts for the process of the invention are secondary or tertiary alcohols and secondary or tertiary diols. Examples of these are diphenylmethanol, t-butanol, sec-butanol, 2-methyl-2-butanol, 3,3-dimethyl-2-butanol, 3-methyl-3-pentanol, 2,4-dimethyl-3-pentanol, 2,4-dimethylpentane-2,4-diol, 2,6-dimethylcyclohexanol, 2,5-dimethylhexane-2,5-diol. The alcohols or diols mentioned are used in a molar ratio of alcohol or diol to 2-haloaldehyde acetal of from 0.01:1 to 20:1, preferably from 0.01:1 to 2.5:1, particularly preferably from 0.01:1 to 0.3:1.

Particularly good results are obtained if in the process of the invention a phase transfer catalyst is used together with a secondary or tertiary alcohol or a primary diol or a secondary or tertiary diol in the amounts indicated above. The combined use of a phase transfer catalyst and a secondary or tertiary alcohol or diol component greatly accelerates the reaction, so that the reaction is completed substantially faster than with the use of only one of the two components.

The process of the invention is preferably carried out in an organic non-alcoholic solvent. Suitable solvents are the aliphatic hydrocarbons usually used in organic chemical synthesis such as n-hexane, halogenated aliphatic hydrocarbons such as methylene chloride, aromatic hydrocarbons such as toluene, halogenated aromatics such as chlorobenzene or ethers such as t-butyl methyl ether, diethyl ether, THF.

The process of the invention is carried out at atmospheric pressure at temperatures of from 0° C. to 200° C., preferably from 20° C. to 130° C., particularly preferably from 20° C. to 80° C. It is not necessary to work under a protective gas. The process can be carried out in the reaction apparatus customary for chemical synthesis, which are fitted with stirrer, reflux condenser, heating/cooling means and, if required, a water separator. The starting materials to be used in the process, such as 2-haloaldehyde acetal, phase transfer catalyst, tertiary alcohol or diol and alkali metal hydroxide or alkaline earth metal hydroxide, can be used as technical grades without any further pretreatment.

The process of the invention can be carried out with all or some of the components of the reaction mixture in the initial charge, or by having only a part initially present and subsequently metering in the remaining component(s) of the reaction mixture. Generally, the 2-haloaldehyde acetal in the solvent is in the initial charge, and the reaction without a solvent is also possible. The alkali metal hydroxide or alkaline earth metal hydroxide component and the catalyst component (phase transfer catalyst and/or secondary or tertiary alcohol (diol)) are generally in the initial charge, but can also be metered in. It is desirable for the reaction that there be good mixing of the two-phase system, which is achieved by vigorous stirring, preferably at a stirring speed of from 300 to 1000 rpm, with a suitable stirrer, for example with a propeller or blade stirrer.

The water formed as a by-product in the process of the invention, which would react further with the ketene acetal product to give the ester and alcohol, is distilled off by continuous azeotropic distillation with a suitable solvent. If the alkali metal hydroxide or alkaline earth metal hydroxide is used in excess, then the water of the reaction is absorbed by the hydroxide component. In this case the azeotropic distillation can be omitted.

The ketene acetals which can be prepared by the process of the invention serve as an intermediate in organic synthesis, for example, as the ene component for Diels-Alder reactions. Cyclic ketene acetals, in particular 2-methylene-1,3-dioxepane, are suitable as monomers or comonomers for free radical polymerization. 2-Methylene-1,3-dioxepane here undergoes a ring opening polymerization, forming a polyester or, in the case of copolymerization with other monomers, a copolymer containing ester groups. Because of the enzymatically cleavable ester groups in the polymer backbone, cyclic ketene acetals are suitable as (co)monomer component for the production of biodegradable plastics.

Other objects and features of the present invention will become apparent from the following detailed description considered in connection with the accompanying Examples, which discloses embodiments of the present invention. It should be understood, however, that the Examples are designed for the purpose of illustration only and not as a definition of the limits of the invention.

DETAILED DESCRIPTION OF PREFERRED EMBODIMENTS

EXAMPLE 1

Preparation of 2-methylene-1,3-dioxepane 80 g (1.2 mol) of finely ground potassium hydroxide (85% pure) were suspended in 500 ml of toluene in a two-liter three neck flask fitted with precision glass stirrer, water separator, reflux condenser and thermometer, and heated to reflux while stirring. After 9.6 ml of the water contained in the potassium hydroxide had separated out, 150.6 g (1.0 mol) of 2-chloromethyl-1,3-dioxepane and 175.4 g ( 1.2 mol) of 2,5-dimethylhexane-2,5-diol were added and the heterogeneous reaction mixture was heated under reflux with vigorous stirring (500 rpm) for eight hours. During this time 18.3 ml of water separated out in the water separator. The reaction mixture was filtered while still hot and subsequently distilled via a Vigreux column. The main fraction of the 2-methylene-1,3-dioxepane distilled over at from 62° C. to 64° C. (5 kPa), having a purity >99% and giving a yield of 76.8 g (68.4% of theoretical). Including the product contained in the intermediate fraction, the total yield was 98.0 g (86.0% of theoretical). The 2,5-dimethyl-2,5-hexanediol was recovered.

EXAMPLE 2

In an apparatus as in Example 1, but without water separator, a mixture of 600 g (4 mol) of 2-chloromethyl-1,3dioxepane, 20 g (76 mmol) of 18-crown-6, 660 g (10 mol) of finely ground potassium hydroxide (85% pure) and 500 ml of tert.-butyl methyl ether were heated under reflux with vigorous stirring for 10 hours. After cooling, salts and excess base were filtered off and the reaction mixture was distilled. Yield: 184.1 g (40.3% of theoretical).

EXAMPLE 3

The procedure was as in Example 2, 75.3 g (0.5 mol) of 2-chloromethyl-1,3-dioxepane, 150 ml of tert.-butyl methyl ether, 4.0 g of polyethylene glycol 1000 dimethyl ether and 75 g (1.14 mol) of finely ground potassium hydroxide (85% pure) were heated under reflux with stirring for 6.5 hours. After filtration the reaction mixture was distilled. Yield: 9.8 g (17.1% of theoretical).

EXAMPLE 4

The procedure was as in Example 3, except that 11.0 g (125 mmol) of 2-methyl-2-butanol were used instead of 4 g of polyethylene glycol 1000 dimethyl ether. The duration of the reaction was again 6.5 hours. Yield: 16.1 g (28.3% of theoretical).

EXAMPLE 5

The procedure was as in Example 3, except that a further 11 g (125 mmol) of 2-methyl-2-butanol were added to the 4 g of polyethylene glycol 1000 dimethyl ether and that 105 g of potassium hydroxide (85% pure) were used instead of 75 g of potassium hydroxide (85% pure). The duration of the reaction was 3 hours. Yield: 40.5 g (77% of theoretical).

EXAMPLE 6

Preparation of 1,1-diethoxyethene 152.6 g (1 mol) of chloroacetaldehyde diethylacetal, 200 g (3 tool) of potassium hydroxide (85% pure), 8 g of polyethylene glycol 1000 dimethyl ether, 22.0 g (250 mmol) of 2-methyl-2-butanol and 300 ml of tert.-butyl methyl ether were heated under reflux with stirring for four hours. After the reaction had ended the salts were filtered off and the reaction mixture distilled under atmospheric pressure. The product boiled at 125° C. (100 kPa). Yield: 89.3 g (77% of theoretical).

COMPARATIVE EXAMPLE 1

The procedure was as in Example 1, except that no 2,5-dimethyl-2,5-hexanediol was added. The sole product-containing fraction yielded 16.1 g of a mixture of 25.2% of 2-methylene-1,3-dioxepene (equals 4.05 g), 37.0% of 2-chloromethyl-1,3-dioxepene and 37.8% of toluene. The conversion was therefore 3.5% of theoretical.

COMPARATIVE EXAMPLE 2

The procedure was as in Example 2, except that no phase transfer catalyst (18-crown-6) was used. The sole product-containing fraction yielded 18 g of a mixture of 29% of 2-methylene-1,3-dioxepane (equals 5.2 g) and 71% of 2-chloromethyl-1,3-dioxepane. The conversion was therefore 1.14% of theoretical.

EXAMPLE 7

Preparation of 2-methylene-1,3-dioxepane 361.5 g (2.4 mol) of 2-chloromethyl-1,3-dioxepane, 720 ml of tert.-butyl methyl ether, 40 g of polyethylene glycol 1000 dimethyl ether, 100 g (0.25 mol) of 2-methyl-2-butanol and 500 g (7.5 mol) of technical grade potassium hydroxide (91%) were heated to reflux while stirring. After 6 hours of reaction time, the reaction was stopped, the salts filtered off, the solvent distilled at atmospheric pressure and the product distilled at 5 kPa. The yield of pure 2-methylene-1,3-dioxepane was 81.4% of theoretical, while the product contained in the intermediate fractions of the total yield was 96.3% of theoretical.

EXAMPLE 8

Preparation of 1,1-dipropoxyethene 270.8 g (1.5 mol) of 1-chloro-2,2-dipropoxyethane, 450 ml of tert.-butyl methyl ether, 19.8 g (0.22 mol) of 2-methyl-2-butanol, 12 g of polyethylene glycol-1000 dimethyl ether and 300 g (4.5 mol) of technical grade potassium hydroxide (91%) were heated under reflux while stirring for six hours. The reaction was stopped, the salts filtered off and the product distilled. The conversion was 86.3% of theoretical. The main fraction contained 148.1 g (68.6% of theoretical) of pure 1,1-dipropoxyethene (b.p. 70° C. at 1.2 kPa).

EXAMPLE 9

Preparation of 1,1-dibutoxyethene 209 g (1 mol) of 1-chloro-2,2-dibutoxyethane, 300 ml of tert.-butyl methyl ether, 13.2 g (0.13 mol) of 2-methyl-2-butanol, 8 g of polyethylene glycol 1000 dimethyl ether and 200 g (3 mol) of technical grade potassium hydroxide were heated under reflux while stirring for six hours. The reaction mixture was worked up as described above. The conversion was 77.1% of theoretical, the yield of pure material was 60.8% of theoretical (b.p. 87°–88° C., 1.5 kPa).

EXAMPLE 10

Preparation of 1,1-diethoxyethene 610.4 g (4.0 mol) of chloroacetaldehyde diethyl acetal, 800 g (12.0 mol) of powdered technical grade potassium hydroxide, 32 g of polyethylene glycol 1000 dimethyl ether and 88 g (1.0 mol) of 2-methyl-2-butanol were heated to reflux in 1.2 l of tert.-butyl methyl ether while stirring. After six hours the reaction was stopped, the salts filtered off and the reaction mixture distilled at reduced pressure (5 kPa). 326 g (72.5% of theoretical) of 1,1-diethoxyethene (b.p. 49° C./5 kPa) were obtained.

EXAMPLE 11

Preparation of 2-methylene-1,3-dioxepane) (pilot plant scale)

70 kg (464.7 mol) of 2-chloromethyl-l,3-dioxepane, 96.8 kg (1451 mol) of technical grade potassium hydroxide (powdered), 7.8 kg of polyethylene glycol 1000 dimethyl ether and 19.4 kg (48.5 mol) of 2-methyl-2-butanol in 116 kg of tert.-butyl methyl ether were heated in an 800 l V4A agitated vessel fitted with a reflux condenser for 6 hours under reflux. After cooling the reaction mixture was diluted with 164 kg of tert.-butyl methyl ether and separated from salts and excess base by filtration with a pressure filter.

Examination of the reaction mixture by gas chromatography showed an almost quantitative conversion of 2-chloromethyl-1,3-dioxepane. The crude yield of 2-methylene-1,3-dioxepane was 93.7% of theoretical. Distillation at reduced pressure gave 43.7 kg (82.4% of theoretical) of 2-methylene-1,3-dioxepane (b.p. 60°–61° C. at 3 kPa) with a purity according to gas chromatography of greater than 99%.

EXAMPLE 12

150.6 g (1.0 mol) of 2-chloromethyl-1,3-dioxepane, 200.0 g (3.0 mol) of technical grade potassium hydroxide (powdered), 8.0 g of polyethylene glycol 1000 dimethyl ether and 25.5 g (0.25 mol) of 3,3-dimethyl-butan-2-ol were heated under reflux in 300 ml of tert.-butyl methyl ether while stirring for 6 hours. The salts were subsequently separated off and the tert.-butyl methyl ether was distilled off. The conversion of 2-chloromethyl-1,3-dioxepane was 97.2% and the yield of 2-methylene-13-dioxepane was 71.7%.

EXAMPLE 13

The procedure was as in Example 12, except that 29.0 g (0.25 mol) of 2,4-dimethylpentan-3-ol were used instead of the 3,3-dimethylbutan-2-ol. The conversion of 2-chloromethyl-1,3-dioxepane was 96.8% and the yield of 2-methylene-1,3-dioxepane was 77.8%.

EXAMPLE 14

The procedure was as in Example 12, except that 32.0 g (0.25 mol) of 2,6-dimethylcyclohexanol were used instead of the 3,3-dimethylbutan-2-ol. The conversion of 2-chloromethyl-1,3-dioxepane was 97.4% and the yield of 2-methylene-1,3-dioxepane was 87.9%.

While several examples of the present invention have been presented, it is to be understood that many changes and modifications may be made thereunto without departing from the spirit and scope of the invention as defined in the appended claims.

What is claimed is:

1. A process for preparing ketene acetals by dehydrohalogenation of an open chain or cyclic 2-haloaldehyde acetal, comprising a) whenever said acetal is an open chain 2-haloaldehyde acetal, carrying out dehydrohalogenation in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a secondary diol, a tertiary diol and the mixtures thereof; and b) whenever said acetal is cyclic 2-haloaldehyde acetal, carrying out dehydrohalogenation in the presence of a hydroxide selected from the group consisting of an alkali metal hydroxide and an alkaline earth metal hydroxide and a phase transfer catalyst, and optionally, another substance selected from the group consisting of a secondary alcohol, a tertiary alcohol, a secondary diol and tertiary diol, or whenever said acetal is cyclic 2-haloaldehyde, carrying out the dehydrohalogenation in the presence of a hydroxide selected from the group consisting of an alkali metal hydroxide and alkaline earth metal hydroxide and a compound selected from the group consisting of a secondary diol and a tertiary diol.

2. The process as claimed in claim 1, wherein the open chain or cyclic 2-haloaldehyde acetal used as a starting material has the formula

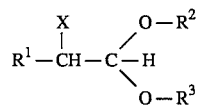

or

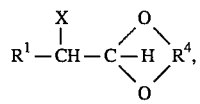

in which $R^1$ is hydrogen, a straight chain, branched or cyclic alkyl having from 1 to 18 carbon atoms, alkenyl having from 2 to 18 carbon atoms, aryl having from 6 to 12 carbon atoms, or aralkyl having from 7 to 12 carbon atoms;

$R^2$ and $R^3$ are the same or different and are alkyl having from 1 to 18 carbon atoms, alkenyl having from 2 to 18 carbon atoms, aryl having from 6 to 12 carbon atoms, or aralkyl having from 7 to 12 carbon atoms; and $R^4$ is $(CR^5R^6)_m$ with m being an integer from 2 to 5, in which $R^5$ and $R^6$ are the same or different and are hydrogen, a straight chain or branched alkyl having from 1 to 4 carbon atoms, alkenyl having from 2 to 4 carbon atoms, aryl having from 6 to 12 carbon atoms, or aralkyl having from 7 to 12 carbon atoms.

3. The process as claimed in claim 2, wherein the starting materials used are 2-haloaldehyde acetals in which X is Cl, $R^1$ is hydrogen, $R^2$ and $R^3$ are the same and are alkyl having from 1 to 4 carbon atoms and $R^4$ is $-(CH_2)_4-$.

4. The process as claimed in claim 1, wherein the alkali metal hydroxide or alkaline earth metal hydroxide is selected from the group consisting of LiOH, NaOH, KOH, CsOH, Ca(OH)$_2$, Sr(OH)$_2$, and Ba(OH)$_2$, in a molar ratio of 2-haloaldehyde acetal to alkali metal hydroxide or alkaline earth metal hydroxide of from 1:1 to 1:25.

5. The process as claimed in claim 4, wherein potassium hydroxide is used in a molar ratio of 2-haloaldehyde acetal to potassium hydroxide of from 1:1 to 1:5.

6. A process for preparing ketane acetals by dehydrohalogenation of an open chain or cyclic 2-haloaldehyde acetal, comprising a) whenever said acetal is an open chain 2-haloaldehyde acetal, carrying out dehydrohalogenation in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a secondary diol, a teritary diol and the mixtures thereof; and b) whenever said acetal is cyclic 2-haloaldehyde acetal, carrying out dehydrohalogenation in the presence of a hydroxide selected from the group consisting of an alkali metal hydroxide and an alkaline earth metal hydroxide and phase transfer catalyst, and optionally, another substance selected from the group consisting of a secondary alcohol, a tertiary alcohol, a secondary diol and tertiary diol, or whenever said acetal is cyclic 2-haloaldehyde, carrying out the dehydrohalogenation in the presence of a hydroxide selected from the group consisting of an alkali metal hydroxide and alkaline earth metal hydroxide and a compound selected from the group consisting of a secondary diol and a tertiary diol; and wherein the phase transfer catalyst used is a compound selected from the group consisting of a polyethylene glycol dialkyl ether, a polyethylene glycol aryl aralkyl ether, a polyethylene glycol alkyl aryl ether, a crown ether, tris-[2-(2-methoxyethoxy)ethyl]amine, a tetraalkylammonium salt, and an aralkyltrialkylammonium salt, in a weight ratio of phase transfer catalyst to 2-haloaldehyde acetal of from 0.001:1 to 1:1.

7. The process as claimed in claim 1, wherein the secondary alcohol or tertiary alcohol or secondary diol or tertiary diol used is selected from the group consisting of diphenylmethanol, t-butanol, sec-butanol, 2-methyl-2-butanol, 3,3-dimethyl-2-butanol, 3-methyl-3-pentanol, 2,4-dimethyl-3-pentanol, 2,4-dimethylpentane-2,4-diol, 2,6-dimethylcyclohexanol, and 2,5-dimethylhexane-2,5-diol, in a molar ratio of alcohol or diol to 2-haloaldehyde acetal of from 0.01:1 to 20:1.

8. The process as claimed in claim 1, wherein the molar ratio of 2-haloaldehyde acetal to alkali metal hydroxide or alkaline earth metal hydroxide is from 1:2 to 1:5 and the molar ratio of 2-haloaldehyde acetal to alcohol or diol component is from 1:0.01 to 1:0.3.

9. A process for preparing an open chain ketene acetal by dehydrohalogenation of an open chain 2-haloaldehyde acetal, comprising carrying out the dehydrohalogenation of the open chain 2-haloaldehyde acetal in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a secondary diol, a tertiary diol, and the mixtures thereof.

10. The process as claimed in claim 9, wherein the open chain 2-haloaldehyde acetal used as starting material has the formula

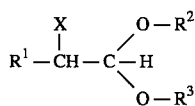

in which $R^1$ is hydrogen, a straight chain, branched or cyclic alkyl having from 1 to 18 carbon atoms, alkenyl having from 2 to 18 carbon atoms, aryl having from 6 to 12 carbon atoms, aralkyl having from 7 to 12 carbon atoms; and $R^2$ and $R^3$ are the same or different and are alkyl having from 1 to 18 carbon atoms, alkenyl having from 2 to 18 carbon atoms, aryl having from 6 to 12 carbon atoms, or aralkyl having from 7 to 12 carbon atoms.

11. The process as claimed in claim 10, wherein the starting materials used are open chain 2-haloaldehyde acetals in which X is Cl, $R^1$ is hydrogen, $R^2$ and $R^3$ are the same and are alkyl having from 1 to 4 carbon atoms.

12. The process as claimed in claim 9, wherein the alkali metal hydroxide or alkaline earth metal hydroxide is selected from the group consisting of LiOH, NaOH, KOH, CsOH, Ca(OH)$_2$, Sr(OH)$_2$, and Ba(OH)$_2$, in a molar ratio of 2-haloaldehyde acetal to alkali metal hydroxide or alkaline earth metal hydroxide of from 1:1 to 1:25.

13. The process as claimed in claim 12, wherein potassium hydroxide is used in a molar ratio of 2-haloaldehyde acetal to potassium hydroxide of from 1:1 to 1:5.

14. A process for preparing an open chain ketene acetal by dehydrohalogenation of an open chain 2-haloaldehyde acetal, comprising carrying out the dehydrohalogenation of the open chain 2-haloaldehyde acetal in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a secondary diol, a tertiary diol, and the mixtures thereof;

wherein the phase transfer catalyst used is a compound selected from the group consisting of a polyethylene glycol dialkyl ether, a polyethylene glycol aryl aralkyl ether, a polyethylene glycol alkyl aryl ether, a crown ether, tris-[2-(2-methoxyethoxy)ethyl]amine, a tetraalkylammonium salt, and an aralkyltrialkylammonium salt, in a weight ratio of phase transfer catalyst to 2-haloaldehyde acetal of from 0.001:1 to 1:1.

15. The process as claimed in claim 9, wherein the secondary alcohol or tertiary alcohol or secondary diol or tertiary diol is selected from the group consisting of diphenylmethanol, t-butanol, sec-butanol, 2-methyl-2-butanol, 3,3-dimethyl-2-butanol, 3-methyl-3-pentanol, 2,4-dimethyl-3-pentanol, 2,4-dimethylpentane-2,4-diol, 2,6-dimethylcyclohexanol, and 2,5-dimethylhexane-2,5-diol, in a molar ratio of alcohol or diol to 2-haloaldehyde acetal of from 0.01:1 to 20:1.

16. The process as claimed in claim 9, wherein the molar ratio of 2-haloaldehyde acetal to alkali metal hydroxide or alkaline earth metal hydroxide is from 1:2 to 1:5 and the molar ratio of 2-haloaldehyde acetal to alcohol or diol component is from 1:0.01 to 1:0.3.

17. A process for preparing cyclic ketene acetal by dehydrohalogenation of cyclic 2-haloaldehyde acetal, comprising carrying out dehydrohalogenation of cyclic 2-haloaldehyde acetal in the presence of a hydroxide selected from the group consisting of an alkali metal hydroxide and an alkaline earth metal hydroxide and a phase transfer catalyst, and optionally another substance selected from the group consisting of a secondary alcohol, a tertiary alcohol, a secondary diol and a tertiary diol, or carrying out the dehydrohalogenation of cyclic 2-haloaldehyde acetal in the presence of a hydroxide selected from the group consisting of an alkali metal hydroxide and alkaline earth metal hydroxide and a compound selected from the group consisting of secondary diol and a tertiary diol.

18. The process as claimed in claim 17, wherein the cyclic 2-haloaldehyde acetal used as the starting material has the formula

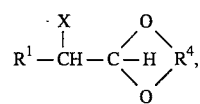

in which $R^1$ is hydrogen, a straight chain, branched or cyclic alkyl having from 1 to 18 carbon atoms, alkenyl having from 2 to 18 carbon atoms, aryl having from 6 to 12 carbon atoms, or aralkyl having from 7 to 12 carbon atoms; and $R^4$ is $(CR^5R^6)_m$ with m being an integer from 2 to 5, in which $R^5$ and $R^6$ may be the same or different and are hydrogen, a straight chain or branched alkyl having from 1 to 4 carbon atoms, alkenyl having from 2 to 4 carbon atoms, aryl having from 6 to 12 carbon atoms, or aralkyl having from 7 to 12 carbon atoms.

19. The process as claimed in claim 18, wherein the starting material used is cyclic 2-haloaldehyde acetal in which X is Cl, $R^1$ is hydrogen, and $R^4$ is —$(CH_2)_4$—.

20. The process as claimed in claim 17, wherein the alkali metal hydroxide or alkaline earth metal hydroxide is selected from the group consisting of LiOH, NaOH, KOH, CsOH, $Ca(OH)_2$, $Sr(OH)_2$, and $Ba(OH)_2$, in a molar ratio of 2-haloaldehyde acetal to alkali metal hydroxide or alkaline earth metal hydroxide of from 1:1 to 1:25.

21. The process as claimed in claim 20, wherein potassium hydroxide is used in a molar ratio of 2-haloaldehyde acetal to potassium hydroxide of from 1:1 to 1:5.

22. The process as claimed in claim 17, wherein the phase transfer catalyst used is a compound selected from the group consisting of a polyethylene glycol dialkyl ether, a polyethylene glycol aryl aralkyl ether, a polyethylene glycol alkyl aryl ether, a crown ether, tris-[2-(2-methoxyethoxy)ethyl] amine, a tetraalkylammonium salt, an aralkyltrialkylammonium salt, in a weight ratio of phase transfer catalyst to 2-haloaldehyde acetal of from 0.001:1 to 1:1.

23. The process as claimed in claim 17, wherein the secondary alcohol or tertiary alcohol or secondary diol or tertiary diol is selected from the group consisting of diphenylmethanol, t-butanol, sec-butanol, 2-methyl-2-butanol, 3,3-dimethyl-2-butanol, 3-methyl-3-pentanol, 2,4-dimethyl-3-pentanol, 2,4-dimethylpentane-2,4-diol, 2,6-dimethylcyclohexanol, 2,5-dimethylhexane-2,5-diol, in a molar ratio of alcohol or diol to 2-haloaldehyde acetal of from 0.01:1 to 20:81.

24. The process as claimed in claim 17, wherein the molar ratio of 2-haloaldehyde acetal to alkali metal hydroxide or alkaline earth metal hydroxide is from 1:2 to 1:5 and the molar ratio of 2-haloaldehyde acetal to alcohol or diol component is from 1:0.01 to 1:0.3.

25. The process as claimed in claim 9,
wherein the phase transfer catalyst is polyethylene glycol dialkyl ether.

26. The process as claimed in claim 25,
wherein the phase transfer catalyst is polyethylene glycol dimethyl ether.

27. The process as claimed in claim 9,
wherein the tertiary diol is 2,5-dimethyl-hexane-2,5-diol.

28. A process for preparing ketene acetals by dehydrohalogenation of an open chain or cyclic 2-haloaldehyde acetal, comprising a) whenever said acetal is an open chain 2-haloaldehyde acetal, carrying out dehydrohalogenation in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a primary diol, a secondary diol, a tertiary diol and the mixtures thereof; and b) whenever said acetal is cyclic 2-haloaldehyde acetal, carrying out dehydrohalogenation in the presence of a hydroxide selected from the group consisting of an alkali metal hydroxide and an alkaline earth metal hydroxide and a phase transfer catalyst, and optionally, another substance selected from the group consisting of a secondary alcohol, a tertiary alcohol, a primary diol, a secondary diol and tertiary diol, or whenever said acetal is cyclic 2-haloaldehyde, carrying out the dehydrohalogenation in the presence of a hydroxide selected from the group consisting of an alkali metal hydroxide and alkaline earth metal hydroxide and a compound selected from the group consisting of a primary diol, a secondary diol and a tertiary diol.

29. The process as claimed in claim 28, wherein the phase transfer catalyst used is a compound selected from the group consisting of a polyethylene glycol dialkyl ether, a polyethylene glycol aryl aralkyl ether, a polyethylene glycol alkyl aryl ether, a crown ether, tris-[2-(2-methoxyethoxy) ethyl ]amine, a tetraalkylammonium salt, and an aralkyltrialkylammonium salt, in a weight ratio of phase transfer catalyst to 2-haloaldehyde acetal of from 0.001:1 to 1:1.

30. A process for preparing an open chain ketene acetal by dehydrohalogenation of an open chain 2-haloaldehyde acetal, comprising carrying out the dehydrohalogenation of the open chain 2-haloaldehyde acetal in the presence of a hydroxide selected from the group consisting of an alkali metal hydroxide and an alkaline earth metal hydroxide and a phase transfer catalyst and another substance selected from the group consisting of a secondary alcohol, a tertiary alcohol, a primary diol, a secondary diol, a tertiary diol, and the mixtures thereof.

31. The process as claimed in claim 30, wherein the phase transfer catalyst used is a compound selected from the group consisting of a polyethylene glycol dialkyl ether, a polyethylene glycol aryl aralkyl ether, a polyethylene glycol alkyl aryl ether, a crown ether, tris- [2-(2-methoxyethoxy)ethyl] amine, a tetraalkylammonium salt, and an aralkyltrialkylammonium salt, in a weight ratio of phase transfer catalyst to 2-haloaldehyde acetal of from 0.001:1 to 1:1.

\* \* \* \* \*